United States Patent
Kawagishi et al.

(10) Patent No.: US 6,626,833 B2
(45) Date of Patent: Sep. 30, 2003

(54) ULTRASONIC DIAGNOSIS SYSTEM

(75) Inventors: Tetsuya Kawagishi, Minato-ku (JP); Yoshitaka Mine, Minato-ku (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/799,025

(22) Filed: Mar. 6, 2001

(65) Prior Publication Data
US 2001/0020131 A1 Sep. 6, 2001

(30) Foreign Application Priority Data

Mar. 6, 2000 (JP) ........................ 2000-060187

(51) Int. Cl.[7] ................................ A61B 8/00
(52) U.S. Cl. ...................................... 600/443
(58) Field of Search ................ 600/437, 443, 600/447, 458; 73/625–626

(56) References Cited

U.S. PATENT DOCUMENTS

| | | | | |
|---|---|---|---|---|
| 4,437,348 A | * | 3/1984 | Sasaki | 73/625 |
| 5,143,075 A | * | 9/1992 | Ishizuka | 600/447 |
| 5,379,642 A | * | 1/1995 | Reckwerdt et al. | 73/625 |
| 5,675,554 A | * | 10/1997 | Cole et al. | 367/138 |
| 5,916,169 A | * | 6/1999 | Hanafy et al. | 600/459 |
| 5,957,852 A | * | 9/1999 | Hossack et al. | 600/458 |
| 6,005,827 A | * | 12/1999 | Hossack et al. | 367/7 |
| 6,104,670 A | * | 8/2000 | Hossack et al. | 367/7 |
| 6,108,572 A | * | 8/2000 | Panda et al. | 600/407 |
| 6,146,330 A | | 11/2000 | Tujino et al. | 600/443 |
| 6,168,565 B1 | * | 1/2001 | Napolitano | 600/447 |

FOREIGN PATENT DOCUMENTS

| | | |
|---|---|---|
| JP | 61-6398 | 2/1986 |
| JP | 11-290318 | 10/1999 |

\* cited by examiner

*Primary Examiner*—Francis J. Jaworski
(74) *Attorney, Agent, or Firm*—Oblon, Spivak, McClelland, Maier & Neustadt, P.C.

(57) ABSTRACT

An ultrasonic diagnosis apparatus has an ultrasonic probe having a plurality of arrayed transducer elements, a transmitting beam former for generating driving signals for driving transducer elements, and a receiving beam former for generating receiving signals based on echo signals received by transducer elements. The transmitting beam former generates driving signals so that phases of ultrasonic waves generated from transducer elements are aligned at multiple focal points. An image processor extracts harmonic components from receiving signals of ultrasonic waves having multiple focal points, and generates ultrasonic image data based on the harmonic components.

17 Claims, 11 Drawing Sheets

ULTRASONIC DIAGNOSIS SYSTEM

CROSS-REFERENCE TO RELATED APPLICATIONS

This application is based upon and claims the benefit of priority from the prior Japanese Patent Application No. 2000-060187, filed Mar. 6, 2000, the entire contents of which are incorporated herein by reference.

BACKGROUND OF THE INVENTION

The present invention relates to an ultrasonic diagnosis apparatus generating an ultrasonic wave image based on harmonic components of ultrasonic waves.

When ultrasonic waves propagate through a system, the waveform is distorted by a nonlinear effect. By this, a harmonic component is generated. Also, when ultrasonic waves hit a microbubble (ultrasonic contrast agent), the microbubble oscillates nonlinearly and collapses. And, at this moment, the harmonic component is generated.

The mechanism of generating harmonic components is given approximately by an equation as the square of an amplitude of the fundamental wave component. Because of this, the harmonic component is generated effectively in a high sound pressure zone. Therefore, compared with basic wave imaging, harmonic imaging is affected less by side lobe and excellent in aerial resolution.

However, compared with basic wave imaging, harmonic imaging tends to make contrast nonuniform. The cause, as described above, is that harmonic components are generated very much at ultrasonic focal points with high sound pressures and their peripheral zones, and on the other hand, they are not generated much in zones far from the focal points. Also, another cause is that, because of attenuation, harmonic components are generated rather much in shallow zones far from focal points, and on the other hand, they are not generated much in deep zones.

BRIEF SUMMARY OF THE INVENTION

It is an object of the present invention to generate an image with relatively uniform contrast between a near distance and a view field depth.

An ultrasonic diagnosis apparatus has an ultrasonic probe having a plurality of arrayed transducer elements, a transmitting beam former for generating driving signals for driving transducer elements, and a receiving beam former for generating receiving signals based on echo signals received by transducer elements. The transmitting beam former generates driving signals so that phases of ultrasonic waves generated from transducer elements are aligned at multiple focal points. An image processor extracts harmonic components from receiving signals of ultrasonic waves having multiple focal points, and generates ultrasonic image data based on the harmonic components.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
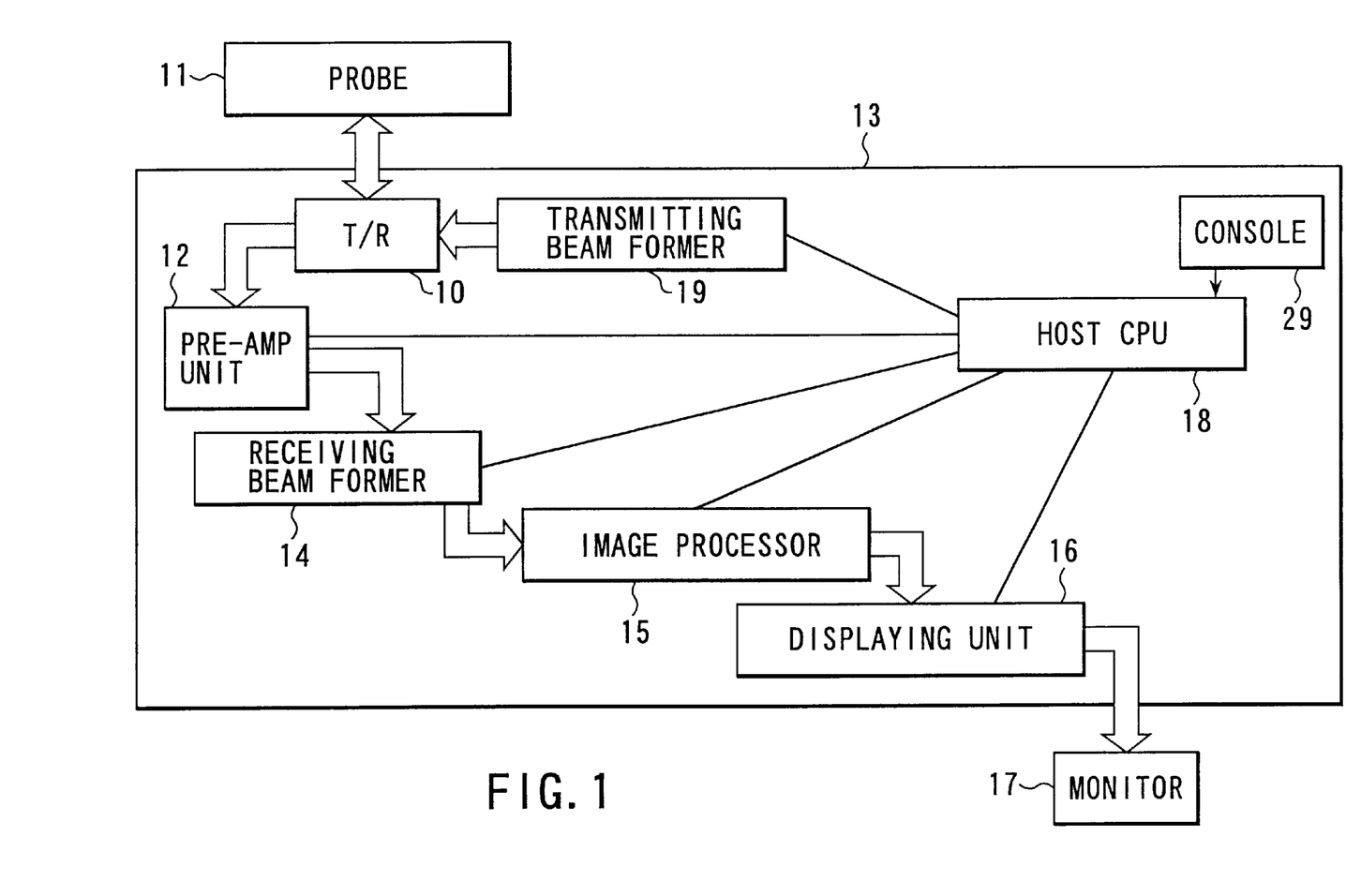
FIG. 1 is a composition drawing of an ultrasonic diagnosis apparatus in an embodiment of the present invention.

The present invention is described in the following by showing a preferable embodiment, referencing drawings. As shown in FIG. 1, an ultrasonic probe 11 and a monitor 17 are connected to a main body of an ultrasonic diagnosis apparatus. The ultrasonic probe 11 has a plurality of transducer elements. As the plurality of transducers, typically, piezo-elements are used. The plurality of transducer elements are arrayed in one-dimensional or two-dimensional form. When the plurality of transducer elements are arrayed in two-dimensional form, the plurality of transducer elements are arrayed in a square or a circle for an entire shape, typically. As the monitor 17, either a CRT or a LCD is used.

The main body 13 has a host CPU 18 for controlling the whole. A transmitting beam former 19, a pre-amp unit 12, a receiving beam former 14, an image processor 15 and a display unit 16 are connected to the host CPU 18.

When transmitting ultrasonic waves, the transmitting beam former 19 is connected to the ultrasonic probe 11. In echo receiving, the receiving beam former 14 is connected to the ultrasonic probe 11 by way of the pre-amp unit 12. Switching of these connections is done by a T/R switch 10.

Figure 2:
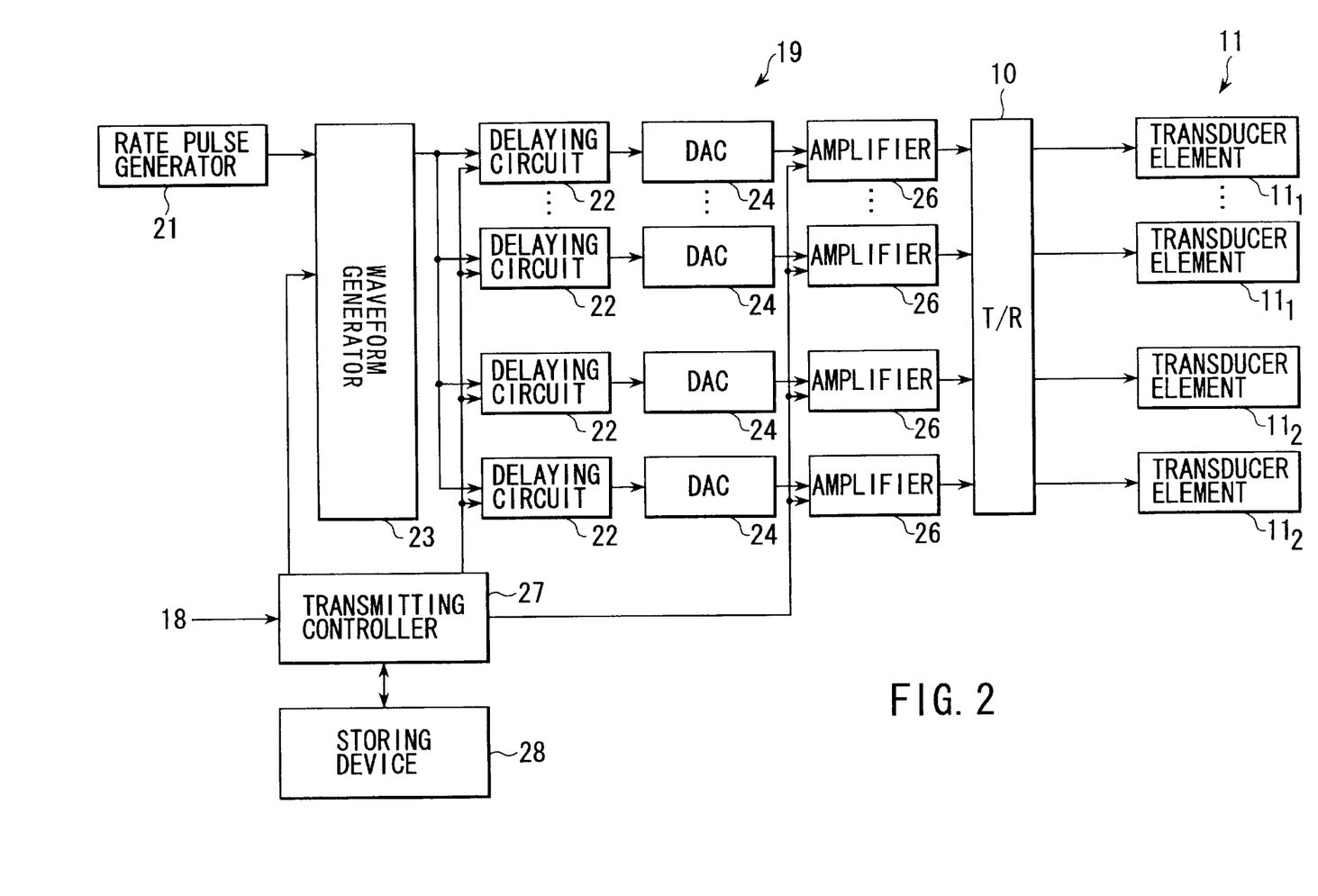
FIG. 2 is a composition drawing of the transmitting beam former of FIG. 1 in the embodiment of the present invention.

FIG. 2 shows a composition of the transmitting beam former 19. A rate pulse generator 21 generates rate pulses at predetermined cycles. Based on the rate pulses, ultrasonic waves are transmitted repeatedly at predetermined cycles. A waveform generator 23 is connected to an output of the rate pulse generator 21. The waveform generator 23 outputs waveform data in accordance with the rate pulse rate from the pulse generator 21. A plurality of delaying circuits 22 are connected to an output of a waveform generator 23. The plurality of delaying circuits 22 respectively correspond to a plurality of transducer elements 11. The each delaying circuit 22 delays a waveform data from the waveform generator 23. A delay time of the each delaying circuit 22 is variable and set individually by control by a transmitting controller 27.

The transmitting controller 27 controls delay times of delaying circuits 22 so as to draw ultrasonic waves generated from a plurality of transducer elements 11 into a beam form and deflect the ultrasonic beam in an optional direction, and so as to make phases of the ultrasonic waves generate almost at the same time from a plurality of transducer elements 11 become the same on a plurality of focal points with different depths, or in short, controls delay times of delaying circuits 22 so as the ultrasonic waves generated almost at the same time from a plurality of transducer elements 11 form a plurality of focal points with different depths. The delay time data necessary for this delay time control are linked with transmitting conditions, including a deflection angle and depths of a plurality of focal points, and stored in a storing device 28, such as ROM. The transmitting controller 27 reads delay time data in accordance with transmitting conditions inputted by way of a console 29 or reads delay time data optimaized in accordance with CHI (contrast harmonic imaging) or THI (tissue harmonic imaging) mode, such as depths of a plurality of focal points, from the storing device 28.

A plurality of digital-to-analog converters 24 are connected respectively to a plurality of waveform generators 23. A plurality of amplifiers 26 are connected respectively to outputs of a plurality of digital-to-analog converters 24. The amplifier 26 amplifies an analog waveform signal outputted from the digital-to-analog converter 24 and outputs a high-frequency voltage signal (henceforth simply referred to as a driving signal) for oscillating the transducer element 11. The transducer element 11 applied with a driving signal oscillates a frequency of the driving signal. By this, ultrasonic waves, having the frequency of the driving signal as a central frequency (henceforth referred to as a fundamental frequency f0), are generated.

The ultrasonic waves generated from the transducer element 11 propagate through inside a specimen. The ultrasonic waves scatter at a border of acoustic impedance in the specimen. A backward scattering is received by a probe 11 as an echo. Incidentally, a frequency component centering around the fundamental frequency f0 is called a fundamental wave component.

Also, when ultrasonic waves propagate through a system, the waveform is distorted by a nonlinear effect. By this, the frequency component centering around the fundamental frequency f0, namely a harmonic component is generated. Also, when a microbubble (ultrsonic contrast agent) is injected in the specimen, the microbubble oscillates nonlinearly and collapses. And, at this moment, the harmonic component is generated. The harmonic component is also received together with the fundamental wave component by the probe 11. Incidentally, although descriptions are given as imaging is done based on a two-dimensional harmonic component centering around a frequency twice the fundamental frequency f0 in the following, of course, imaging may be done based on a higher harmonic component, such as third or fourth harmonic component around a frequency three times of four times the fundamental frequency f0, or by combining secondary and higher harmanic components.

When receiving an echo, the transducer element 11 oscillates mechanically according to the frequency. By this mechanical oscillation, a plurality of electric signals (called receiving signals) are generated. These plurality of receiving signals are sent to the receiving beam transformer by way of the T/R switch 10 and the pre-amp unit 12. The receiving beam former 14 give and add to each receiving signal a delay time according to a receiving directional aity and a focal deep. By this, one echo signal is generated. The image processor 15 generates ultrsonic image data based on a plurality of echo signals that are collected by electronic scanning and differ in directionality. In harmonic imaging, the image processor 15 extracts harmonic components from echo signals, and based on the harmonic components, generates harmonic image data by B mode processing for determining a mode information of a system, CFM processing for determining a shift speed information of a blood flow or the system and the like. Image data generated by the image processor 15 is scan-converted into video signals by the display unit 16, and displayed as an image on the monitor 17.

Figure 3:
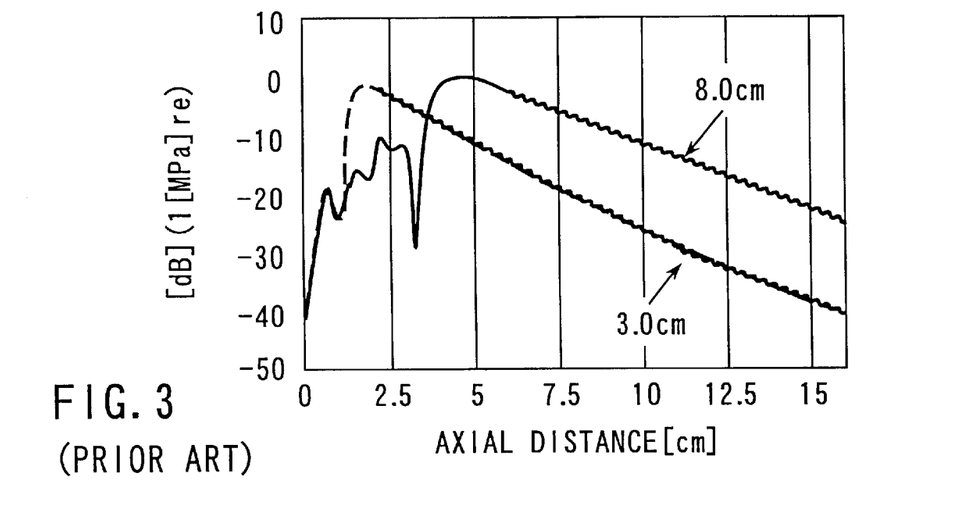
FIG. 3 is a graph showing intensity variations of harmonic components by depths when setting a single focal point at 3 cm and intensity variations of harmonic components by depth when setting the single focal point at 8 cm in a prior art.
Figure 4A:
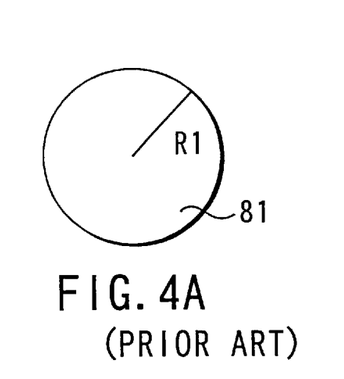
FIG. 4A is a drawing showing a radius of a transmission aperture in the prior art.
Figure 4B:
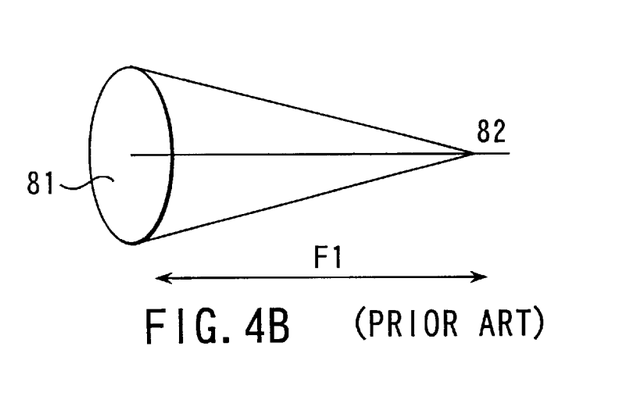
FIG. 4B is a drawing showing the single focal point in the prior art.

As described above, by forming focal points of ultrasonic waves in a plurality of positions with different depths, harmonic components are generated relatively uniformly with regard to the depth direction, compared to forming a focal point of ultrasonic waves in a single position. As shown in FIG. 3, when a focal point is formed at a depth of 3 cm, harmonic components are not generated much in a relatively deep zone of 8 cm or so. Also, when a focal point is formed at a depth of 8 cm, harmonic components are not generated much in a relatively shallow zone of 3 cm or so. As shown in FIG. 4A and FIG. 4B, this distribution of harmonic component generation was measured in a case where driving signals, which were delayed so as to form a single focal point 82 in transducer elements 81 arrayed in circular form, were applied. Like this, harmonic components are generated non-uniformly because of a reason that harmonic components are generated effectively in a zone where the sound pressure of the fundamental wave component is relatively high but are generated a few at all in a zone where the sound pressure of the fundamental wave component is relatively low.

Figure 5A:
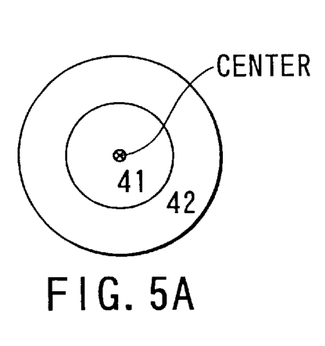
FIG. 5A is a drawing showing an inside zone and an outside zone of transducer elements arrayed in circular two-dimensional form in the embodiment of the present invention.
Figure 5B:
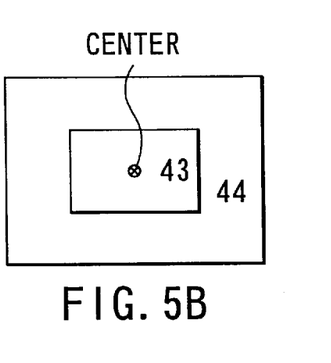
FIG. 5B is a drawing showing an inside zone and an outside zone of transducer elements arrayed in square two-dimensional form in the embodiment of the present invention.
Figure 5C:
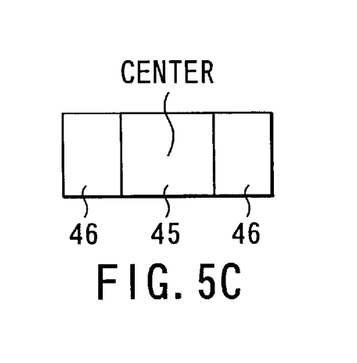
FIG. 5C is a drawing showing an inside zone and an outside zone of transducer elements arrayed in one-dimensional form in the embodiment of the present invention.
Figure 6A:
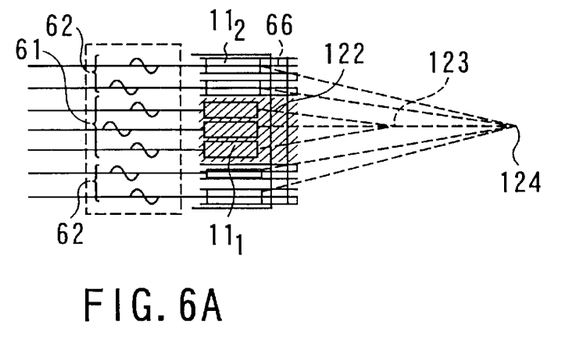
FIG. 6A is a side view of transducer elements arrayed in circular two-dimensional form in the embodiment of the present invention.
Figure 6B:
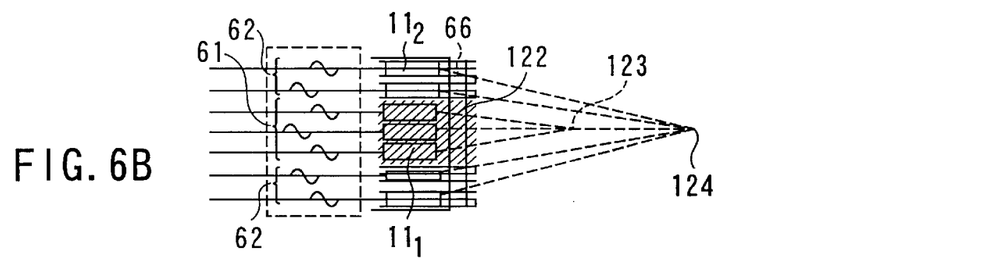
FIG. 6B is a side view of transducer elements arrayed in circular two-dimensional form in the embodiment of the present invention.
Figure 6C:
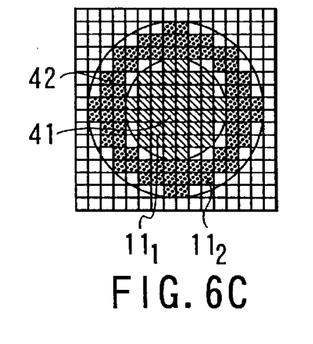
FIG. 6C is a plan view of transducer elements arrayed in circular two-dimensional form in the embodiment of the present invention.
Figure 7A:
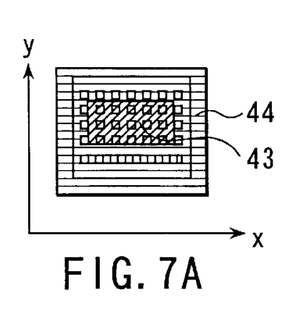
FIG. 7A is a plan view of transducer elements arrayed in square two-dimensional form in the embodiment of the present invention.
Figure 7B:
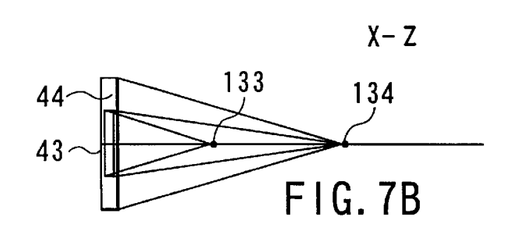
FIG. 7B is a side view of transducer elements arrayed in square two-dimensional form in the embodiment of the present invention.
Figure 7C:
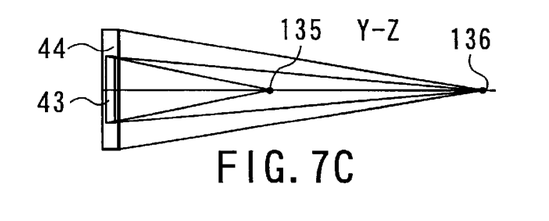
FIG. 7C is a side view of transducer elements arrayed in square two-dimensional form in the embodiment of the present invention.

FIG. 5A, FIG. 5B, and FIG. 5C respectively show a plan view of transducer elements 11 arrayed in circular two-dimensional form, a plan view of transducer elements 11 arrayed in square two-dimensional form, and a plan view of transducer elements 11 arrayed in one dimensional form. As described above, the transmitting beam former 19 generates driving signals so as ultrasonic waves from transducer elements can form a plurality of focal points with different depths. Here, descriptions are given so as two focal points are formed. Of these two focal points, a shallow focal point is called a first focal point, and a deep focal point is called a second focal point. So as the first focal point is formed with a plurality of transducer elements distributed in inner zones 41, 43, and 45 (henceforth referred to as a first transducer element $11_1$), and the second focal point is formed with a plurality of transducer elements distributed in outer zones 42, 44, and 46 located outside the inner zones 41, 43, and 45 (henceforth referred to as a second transducer element $11_2$), the transmitting beam former 19 applies driving signals to the first transducer element $11_1$ and the second transducer element $11_2$ almost at the same time according to the same rate pulse. Incidentally, the first transducer element $11_1$ and the second transducer element $11_2$ are piezoelectric elements having the same thickness, surface shape, and surface area, but called by different names according to their positions of arrangement, merely for the sake of convenience.

As shown in FIG. 5A, the inner zone 41 is set in circular shape centering around a center of an aperture, and the outer zone 42 is set in ring shape having the same center with the inner zone 41. The outer zone 42 is set so as to be enclose the inner zone 41. Also, as shown in FIG. 5B, the inner zone 43 is set in square shape, including a rectangle, centering around a center of an aperture, and the outer zone 44 is set in square shape having the same center with the inner zone 41 and similar to the inner zone 43. The outer zone 44 is set so as to be enclose the inner zone 43. Also, as shown in FIG. 5C, the outer zone 46 is set on both sides of the inner zone 45.

Here, the size and shape of these zones 41, 42, 43, 44, 45 and 46 can easily be changed electrically. That is, since inner zones 41, 43 and 45 merely represent zones where the transducer elements, to which the first driving signal with a delay time given so as to form the shallow first focal point is applied, are distributed, and likewise, since outer zones 42, 44 and 46 merely represent zones where the transducer elements, to which the second driving signal with a delay time given so as to form the deep second focal point is applied, are distributed, the size and shape of zones 41, 42, 43, 44, 45 and 46 can easily be changed respectively by varying the delay time of the delaying circuit 22, which is set by control by the transmitting controller 27.

As shown in FIGS. 6A, 6B and 6C, FIGS. 7A, 7B and 7C, and FIGS. 8A, 8B and 8C, a driving signal 61 applied to the transducer element 111 distributed in inner zones 41, 43 and 45 is given a delay time according to a deflection angle and a delay time necessary for aligning the phase of ultrasonic waves from the transducer element $11_1$ at shallow focal points 123, 133 and 143. A driving signal 62 applied to the transducer element $11_2$ distributed in outer zones 42, 44 and 46 is given a delay time according to the deflection angle and a delay time necessary for aligning the phase of ultrasonic waves from the transducer element $11_2$ at deep focal points 124, 134 and 144.

Figure 8A:
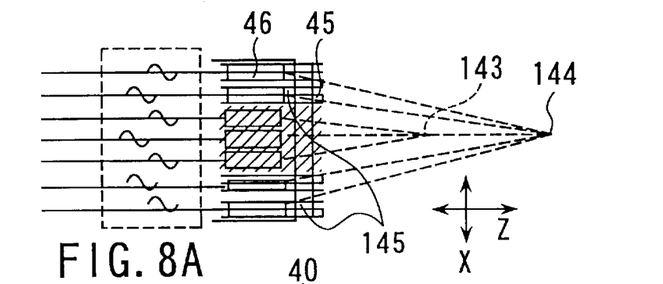
FIG. 8A is a side view of transducer elements arrayed in one-dimensional form in the embodiment of the present invention.
Figure 8B:
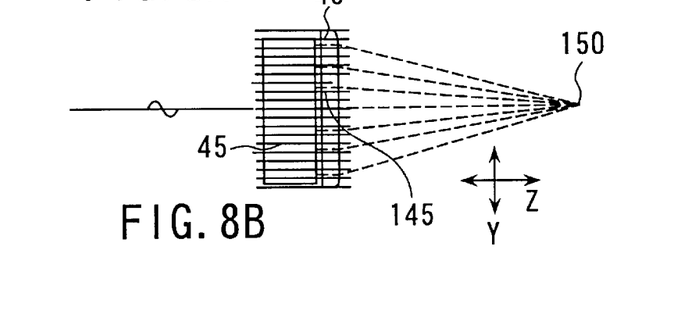
FIG. 8B is a side view of transducer elements arrayed in one-dimensional form in the embodiment of the present invention.
Figure 8C:
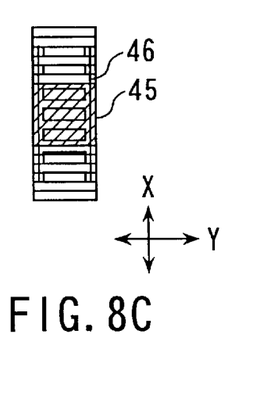
FIG. 8C is a plan view of transducer elements arrayed in one-dimensional form in the embodiment of the present invention.

Incidentally, as shown in FIG. 8B, a focal point 150 is formed with an acoustic lens 40 having a single focal point. Focal points 143 and 50 or 144 and 50 may be the same position or different positions.

Figure 9:
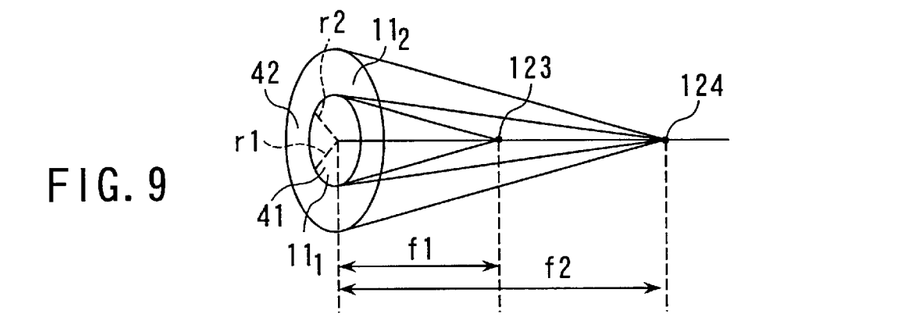
FIG. 9 is a drawing of the two focal points formed by ultrasonic waves from the transducer elements arrayed in circular two-dimensional form in the embodiment of the present invention.
Figure 10:
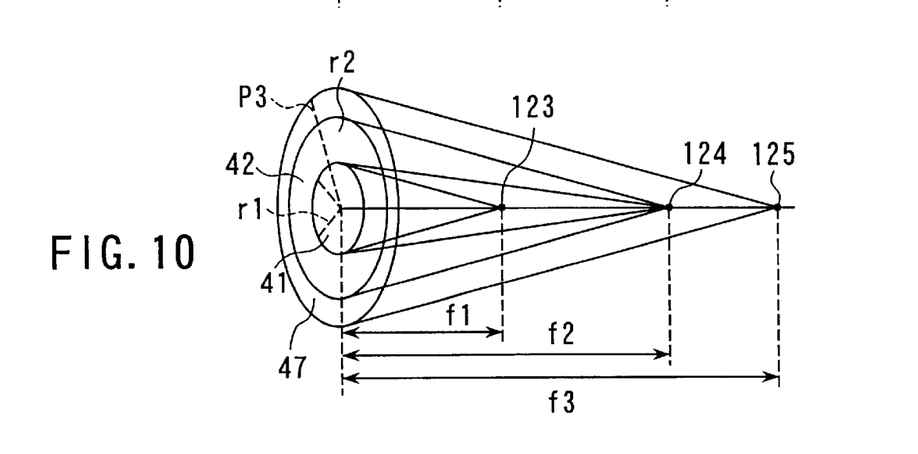
FIG. 10 is a drawing of the three focal points formed by ultrasonic waves from the transducer elements arrayed in circular two-dimensional form in the embodiment of the present invention.

In the following, for the sake of convenience, descriptions are given using a case in which transducer elements 11 are arrayed in circular two-dimensional form (FIG. 5A and FIGS. 6A, 6B and 6C). As shown in FIG. 9, an aperture made up with transducer elements $11_1$ in the inner zone 41 that forms the shallow focal point 123 with a focal distance f1 is called an inner aperture, and an aperture made up with transducer elements $11_2$ in the outer zone 42 that forms the deep focal point 124 with a focal distance f2 is called an outer aperture. A diameter r of the outer aperture is set so as it is longer than a diameter r1 of the inner aperture. Incidentally, as shown in FIG. 10, when forming three (or more than) focal points, a third focal point with a focal distance f3 deeper than the second focal point 124 is formed by the transducer elements 11 in a zone 47 still outside the outer zone 42. A diameter r3 of this transmitting aperture is set so as it is longer than the diameter r2 of the outer aperture.

Figure 11A:
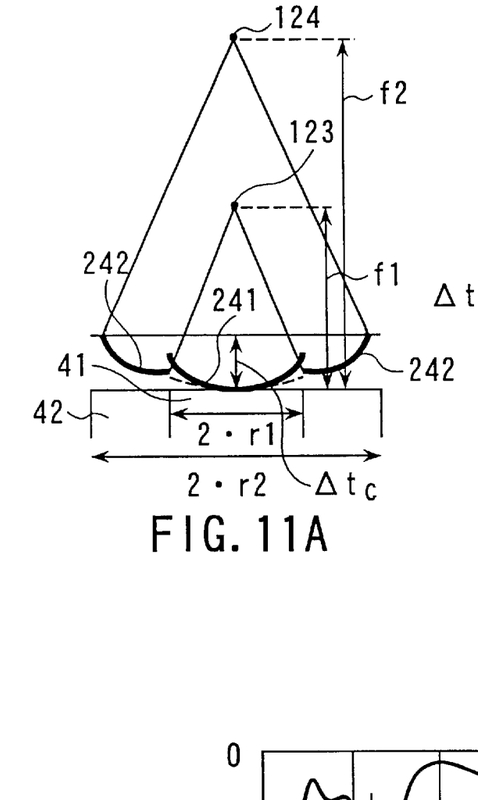
FIG. 11A is a drawing showing a delay curve when no offset delay time is added to a delay time given to a driving signal (first driving signal) of transducer elements that compose an inner aperture for orientation and focusing in the embodiment of the present invention.
Figure 12:
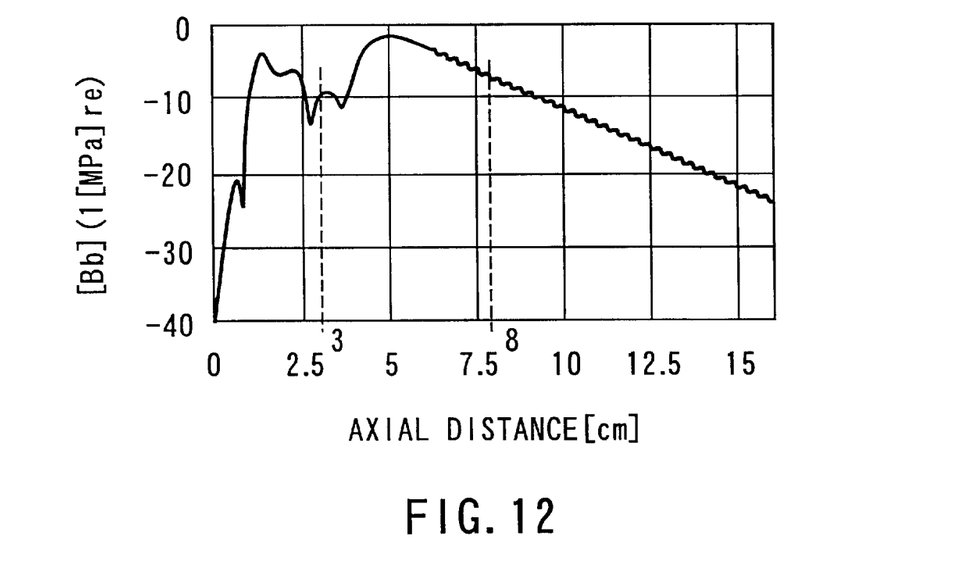
FIG. 12 is a graph showing intensity variations of harmonic components with regard to a distance of an ultrasonic beam on a central axis in the embodiment of the present invention.

As described above, to form the first focal point 123 at the inner aperture and the second focal point 124 at the outer aperture, as shown in FIG. 11A, distribution of a delay time given to driving signals applied to transducer elements $11_1$ that compose the inner aperture 41, namely a curve 241 (a delay curve) connecting the same phase of the driving signals and a delay curve 242 given to driving signals applied to transducer elements composing the outer aperture 42 are set separately based on arcs having focal deeps f1 and f2, respectively. However, initially, the delay curve of the inner aperture and the delay curve of the outer aperture are set so as the delay time of a central position of the inner aperture and the delay time of a central position are the same delay time $\Delta t_c$. In this instance, as shown in FIG. 12, sometimes the intensity of harmonic components generated at the 3 cm depth first focal point 123 is lowered. This occurs with a reason that the phase of ultrasonic waves from the outer aperture 42 is not zero in regard to the phase of ultrasonic waves from the inner aperture 41, namely ultrasonic waves from the outer aperture 42 is not in phase with ultrasonic waves from the inner aperture 41. That is, in the first focal point 123, the intensity of ultrasonic waves from the inner aperture 41 is weakened by ultrasonic waves from the outer aperture 42.

Figure 11B:
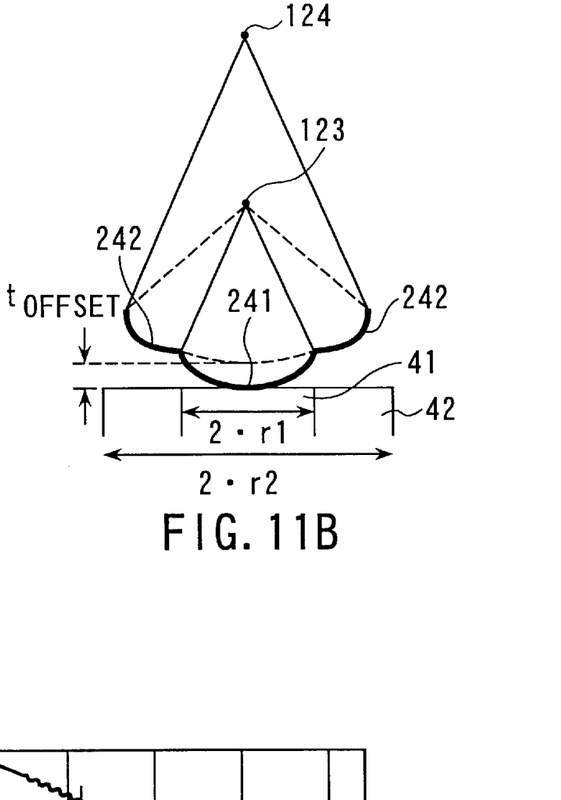
FIG. 11B is a drawing showing a delay curve when an offset delay time is added to the delay time given to the driving signal (first driving signal) of transducer elements that compose the inner aperture for orientation and focusing.
Figure 13A:
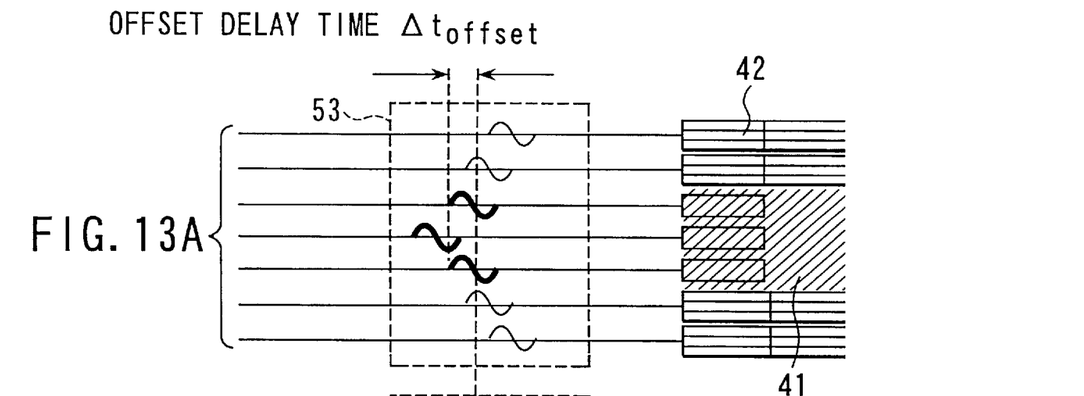
FIG. 13A is a drawing showing driving signals when an offset delay time is added to the delay time given to the driving signal (first driving signal) of transducer elements that compose the inner aperture for orientation and focusing in the embodiment of the present invention.
Figure 13B:
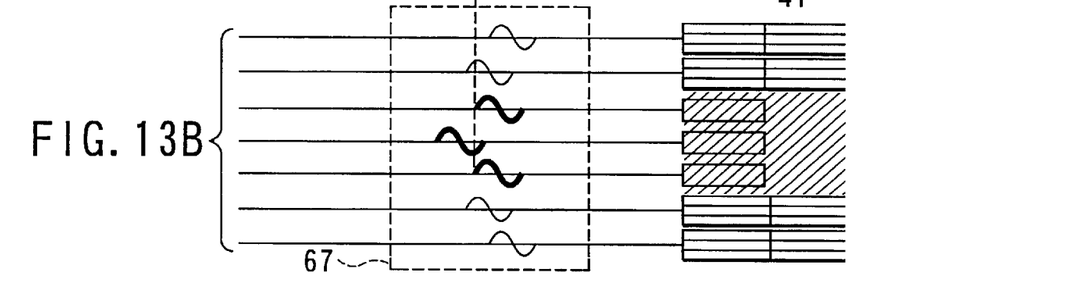
FIG. 13B is a drawing showing driving signals when an offset delay time is added to the delay time given to the driving signal (first driving signal) of transducer elements that compose the inner aperture for orientation and focusing in the embodiment of the present invention.

To solve this, as shown in FIG. 11B and FIGS. 13A and 13B, an offset delay time $\Delta t_{offset}$ is added to a delay time given to driving signals applied to the transducer elements 111 composing the inner aperture 41. By diversely changing the offset delay time $\Delta t_{offset}$ added to the driving signals applied to the transducer elements 111 composing the inner aperture 41, the phase difference of ultrasonic waves from the outer aperture 42 corresponding to ultrasonic waves from the inner aperture 41 can freely be changed at the first focal point 123.

Figure 14:
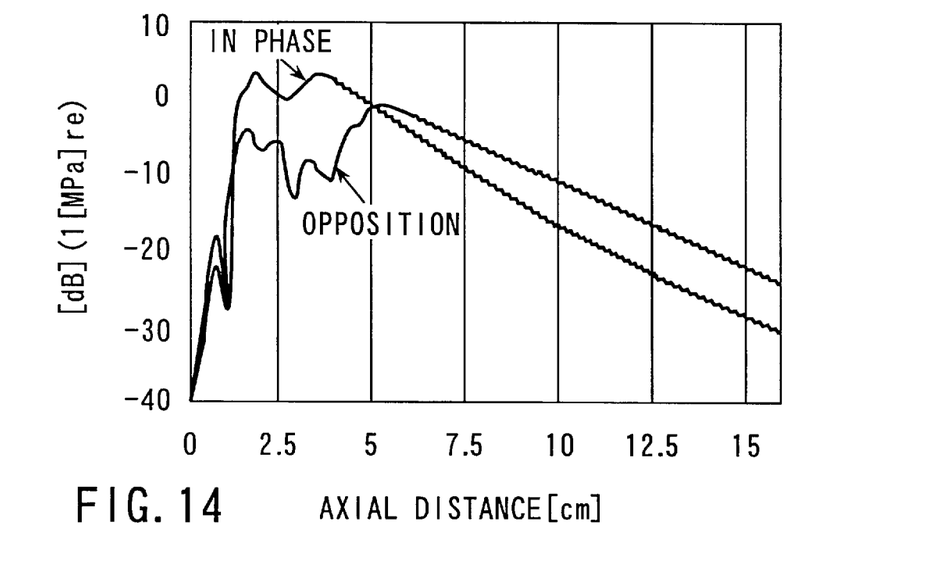
FIG. 14, in the embodiment of the present invention, is a graph showing intensity variations of harmonic components when an offset delay time is given to the driving signal (first driving signal) of transducer elements that compose the inner aperture so that phases of ultrasonic waves of the inner aperture and ultrasonic waves of an outer aperture become the same at a first focal point, and intensity variations of harmonic components when the offset delay time is given to the driving signal (first driving signal) of transducer elements that compose the inner aperture so that phases of ultrasonic waves of the inner aperture and ultrasonic waves of the outer aperture become opposite at the first focal point and the intensity of harmonic components progresses in the depth distance.

For example, by setting the offset delay time $\Delta t_{offset}$ based on aperture diameters r1 and r2, the depth of the first focal point and the fundamental frequency f0 so as the phase difference of ultrasonic waves from the inner aperture 41 corresponding to ultrasonic waves from the outer aperture 42 is zero at the first focal point 123, namely so as ultrasonic waves from the inner aperture 41 are in phase with ultrasonic waves from the outer aperture 42 at the first focal point 123, as shown in FIG. 14, the intensity of harmonic components generated at the first focal point 123 can be maximized.

Figure 15:
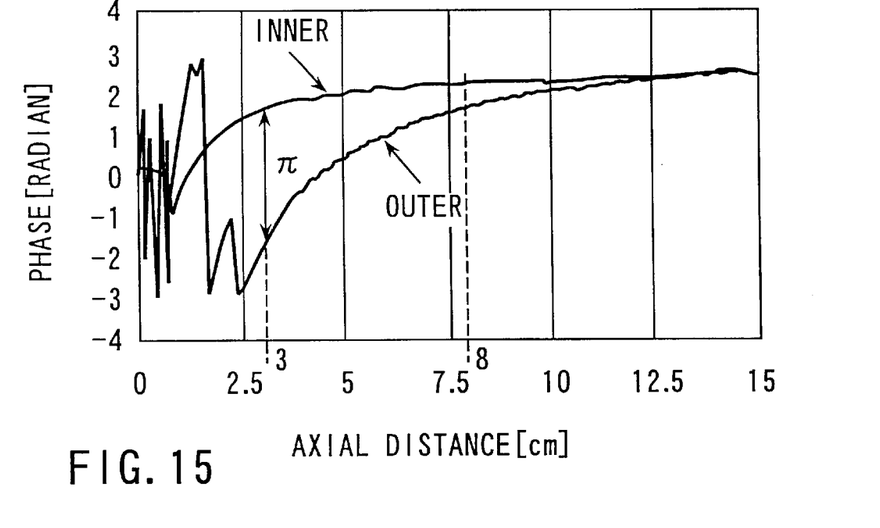
FIG. 15, in the embodiment of the present invention, is a graph showing distance variations in phase difference when an offset delay time is not given to the driving signal (first driving signal) of transducer elements that compose the inner aperture as a result phases of ultrasonic waves of the inner aperture and ultrasonic waves of the outer aperture become opposite at the first focal point and can be increased in the second focal point 124.

Also, as shown in FIG. 15, by setting the offset delay time $\Delta t_{offset}$ so as the phase difference of ultrasonic waves from the inner aperture 41 to ultrasonic waves from the outer aperture 42 is $\pi$, namely so as ultrasonic waves from the inner aperture 41 is in reverse phase from ultrasonic waves from the outer aperture 42 at the first focal point 123, as shown in FIG. 14, the intensity of harmonic components generated at the first focal point 123 can be minimized and can be increased in the second focal point 124.

Further, by setting the offset delay time $\Delta t_{offset}$ so as the phase difference of ultrasonic waves from the inner aperture 41 to ultrasonic waves from the outer aperture 42 is optionally set, the intensity of harmonic components generated at the first focal point 123 can freely be set. For example, the intensity of harmonic components generated at the first focal point 123 can nearly be aligned with the intensity of harmonic components generated at the deep second focal point 124.

A switching of offset delay times like this can be realized by previously storing delay times (data) given various offset delay times in the storing device 28 and by selectively using a specific delay time data according to user instructions related to the intensity of harmonic components of the first focal point inputted by way of the console 29 or delay time data optimaized in accordance with CHI (contrast harmonic imaging) or THI (tissue harmonic imaging) mode. Or, the offset delay time may be calculated by the transmitting controller 27 according to user instructions related to the intensity of harmonic components of the first focal point inputted by way of the console 29.

Figure 16:
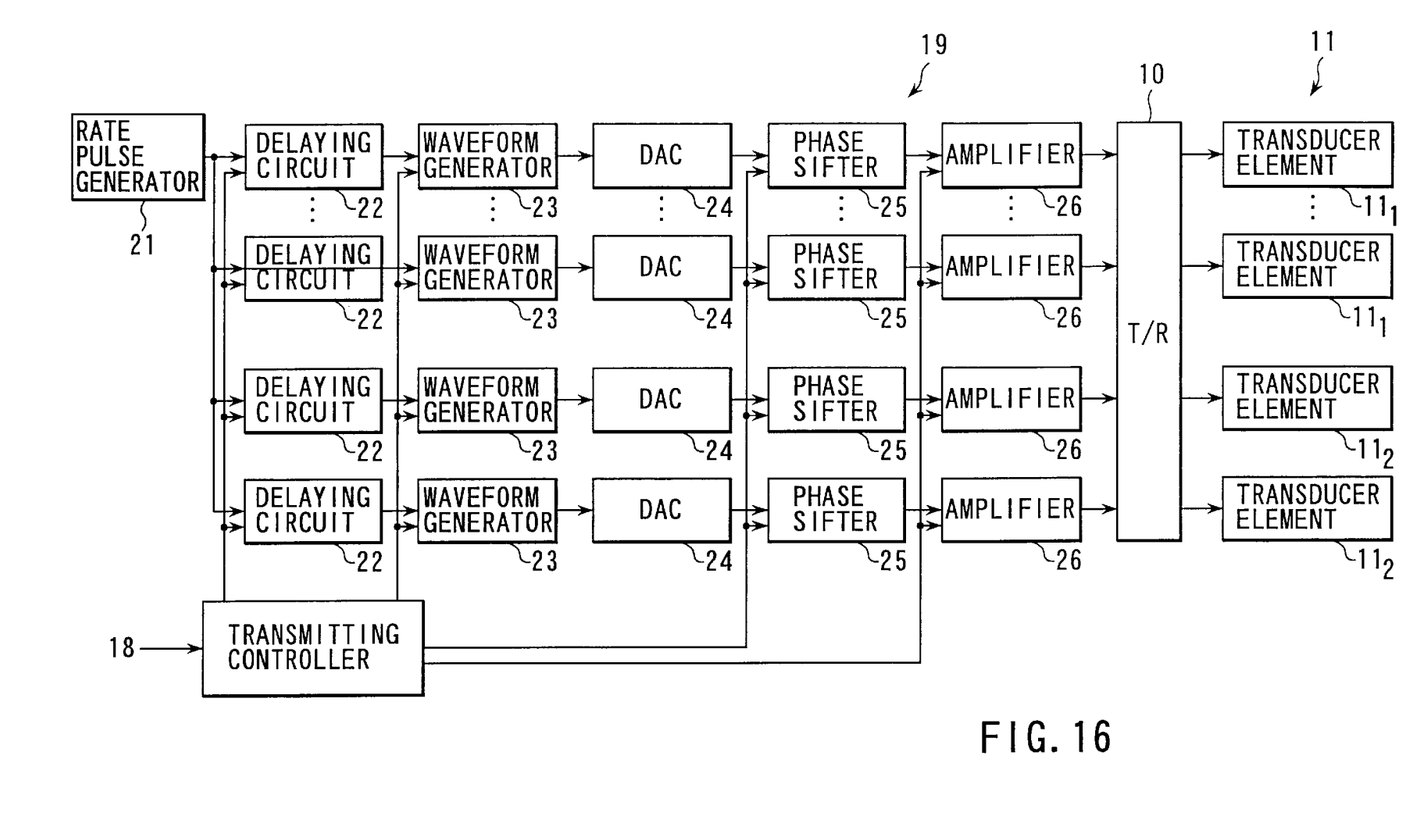
FIG. 16 is a drawing showing a phase shifter for shifting the phase of the driving signal of transducer elements that compose the inner aperture in the embodiment of the present invention.
Figure 17A:
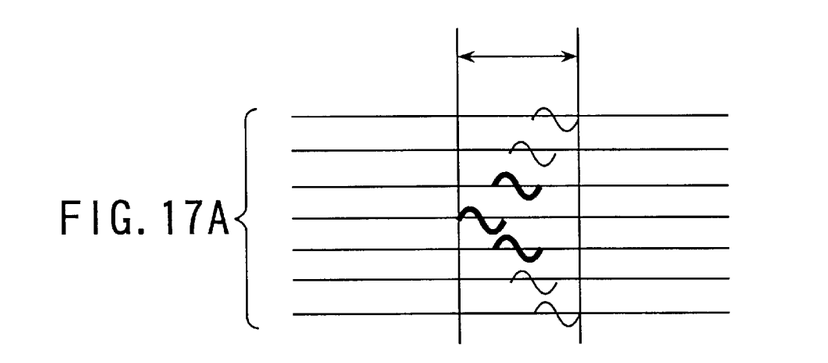
FIG. 17A is a drawing showing the driving signal when the phase of the driving signal applied to transducer elements of the inner aperture is not shifted in the embodiment of the present invention.
Figure 17B:
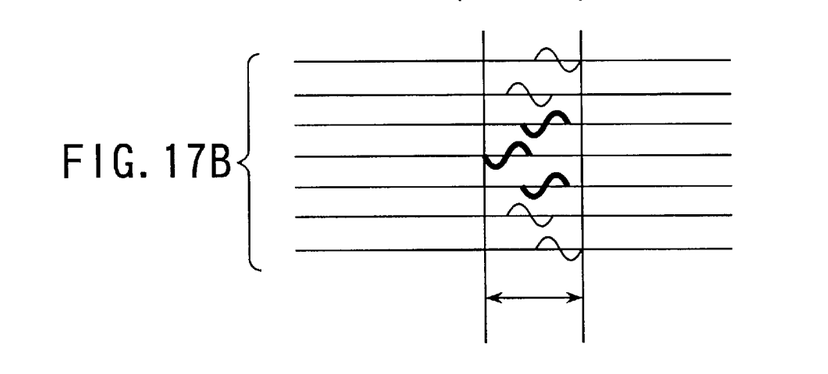
FIG. 17B is a drawing showing the driving signal when the phase of the driving signal applied to transducer elements of the inner aperture is shifted in the embodiment of the present invention.

Additionally, instead of adding an offset delay time to a delay time given to driving signals applied to transducer elements $11_1$ composing the inner aperture 41, the same purpose may be attained by shifting the phase of driving signals applied to transducer elements $11_1$ composing the inner aperture 41. As shown in FIG. 16, this is realized by providing a phase shifter 25 between the DAC 24 and the amplifier 26. The phase shifter 25 shifts the phase of waveform signals as shown in FIGS. 17A and 17B according to a control signal specifying the amount of shift from the transmitting controller. In this instance, the storing device 28 may be not necessary to previously store delay times (data) with given various offset delay times.

Figure 18A:
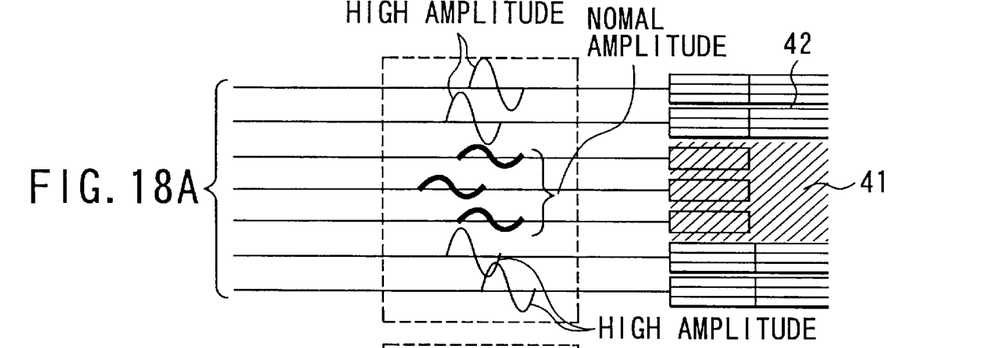
FIG. 18A is a drawing showing a driving signal applied to transducer elements that compose the outer aperture having a higher amplitude than that of the driving signal applied to transducer elements of the inner aperture.
Figure 18B:
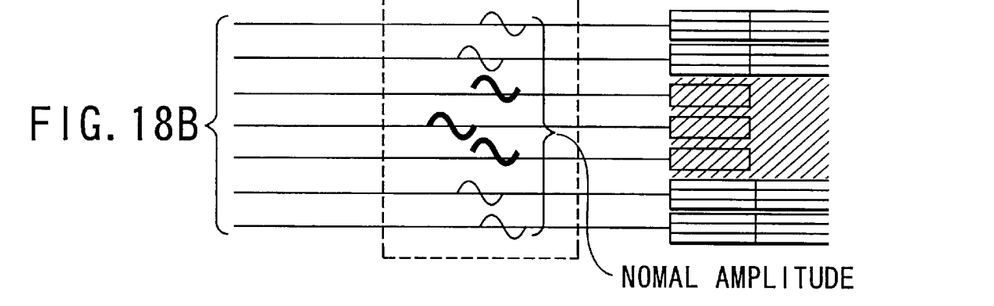
FIG. 18B is a drawing showing a driving signal applied to transducer elements that compose the outer aperture having the same amplitude as that of the driving signal applied to transducer elements of the inner aperture.

Also, as shown in FIG. 18B, when the amplitude of driving signals applied to transducer elements $11_1$ composing the inner aperture 41 is aligned with the amplitude of driving signals applied to transducer elements $11_2$ composing the outer aperture 42, the intensity of harmonic components of the deep second focal point 124 is lower than the intensity of harmonic components of the shallow first focal point 123. To nearly align the intensity of harmonic components between the first focal point 123 and the second focal point 124, as shown in FIG. 18A, the amplitude of driving signals applied to transducer elements 112 composing the outer aperture 42 is set above the amplitude of driving signals applied to transducer elements $11_1$ composing the outer aperture 41, and/or, the amplitude of driving signals applied to transducer elements $11_1$ composing the inner aperture 41 may be set below the amplitude of driving signals applied to transducer elements $11_2$ composing the outer aperture 42. To vary the amplitude, waveform data is switched or the amplification rate of the amplifier 26 is varied by the transmitting controller 27.

By this amplitude control, the generation of cavitations near the near-distance first focal point 123 can be controlled, the intensity of harmonic components near the far-distance second focal point 124 can be raised to improve a view field depth, and favorable for a fever regulation can be acquired.

Figure 19:
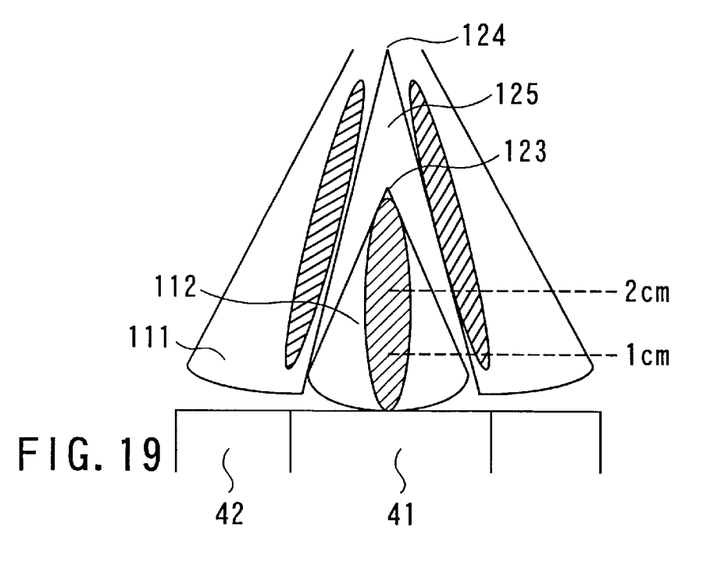
FIG. 19 is a drawing showing a generating zone of harmonic components in the embodiment of the present invention.
Figure 20:
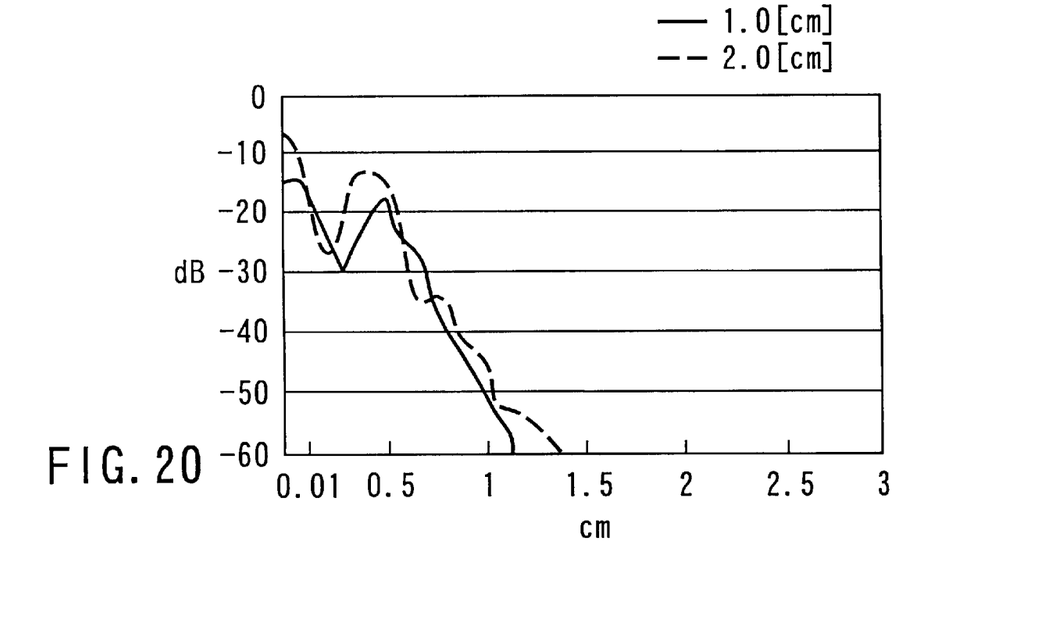
FIG. 20, in the embodiment of the present invention, is a drawing showing intensity variations of harmonic components in a position 1 cm in depth with regard to a distance from the central axis of the ultrasonic beam, and intensity variations of harmonic components in a position 2 cm in depth with regard to the distance from the central axis of the ultrasonic beam.

FIG. 20 shows changes in intensity of harmonic components respectively with regard to a distance from the central axis of ultrasonic beams at positions of 1 cm and 2 cm in deep (see FIG. 19). Harmonic components derived from the fundamental frequency of ultrasonic waves generated from the inner aperture 41 are prominent around 0.1 cm from the central axis. On the other hand, harmonic components derived from the fundamental frequency of ultrasonic waves generated from the outer aperture 42 are prominent around 0.5 cm from the central axis. In other words, a main rope by the inner aperture 41 is formed in near-distance zones, and harmonic components derived from the outer aperture 42 appear like a side rope. A technique for removing the harmonic components (side rope) derived from the outer aperture 42 from receiving signals of these near-distance zones is described below.

Although the frequency of driving signals applied to transducer elements $11_1$ composing the inner aperture 41 (the fundamental frequency of ultrasonic waves generated from the inner aperture 41) is equal with the frequency of driving signals applied to transducer elements $11_2$ composing the outer aperture 42 (the fundamental frequency of ultrasonic waves generated from the outer aperture 42) in the above description, the fundamental frequency of ultrasonic waves generated from the inner aperture 41 and the fundamental frequency of ultrasonic waves generated from the outer aperture 42 may be different.

Figure 21A:
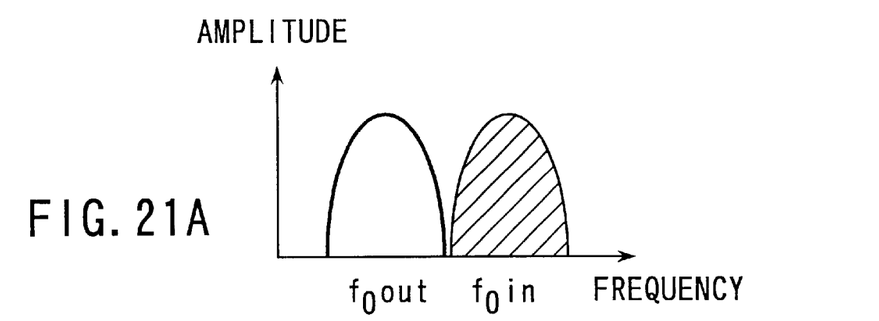
FIG. 21A is a drawing showing a fundamental wave component $f0_{in}$ of ultrasonic waves from the inner aperture and a fundamental wave component $f0_{out}$ of ultrasonic waves from the outer aperture in the embodiment of the present invention.

Typically, as shown in FIG. 21A, each of driving signals is generated so as the fundamental frequency $f0_{out}$ of ultrasonic waves generated from the outer aperture 42 is lower than the fundamental frequency $f0_{in}$ of ultrasonic waves generated from the inner aperture 41. Incidentally, although the fundamental frequency $f0_{in}$ and the fundamental frequency $f0_{out}$ are illustrated as the frequency distributions centering around their centers are completely separated, these may be overlapped. To change the frequency, the waveform data is changed by the transmitting controller 27.

Figure 21B:
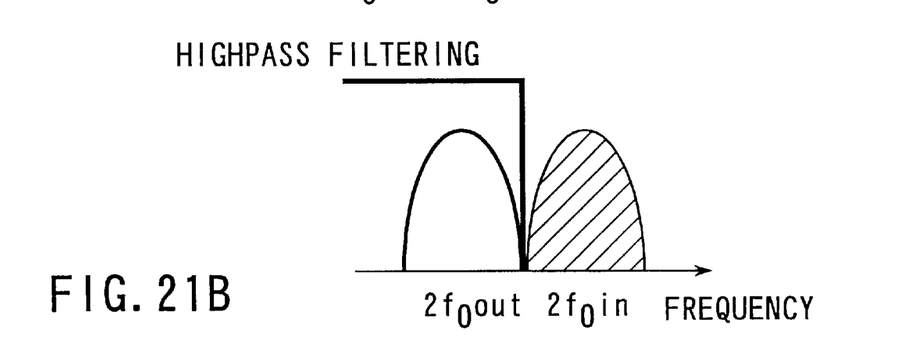
FIG. 21B is a drawing showing a harmonic component $2.f0_{in}$ in derived from ultrasonic waves from the inner aperture and a harmonic component $2.f0_{out}$ of ultrasonic waves from the outer aperture in the embodiment of the present invention.

FIG. 21B shows the two-dimensional harmonic components $2.f0_{in}$ derived from ultrasonic waves generated from the inner aperture 41 contained in receiving signals and the two-dimensional harmonic components $2.f0_{out}$ derived from ultrasonic waves generated from the outer aperture 42 contained in receiving signals. To extract harmonic components $2.f0_{in}$ and remove harmonic components $2.f0_{out}$ from receiving signals of near-distance zones, the image processor 15 provides a highpath filter that functions with a filtering characteristic having a cut-off frequency between $2.f0_{in}$ and $2.f0_{out}$. To pass near-distance receiving signals and not to pass far-distance receiving signals through this highpath filter, a bypath line is provided with a switch in the highpath filter. In order for the switch to shift at a time corresponding to an intermediate deep of the first focal point and the second focal point, the switch is controlled by the host CPU 18. Instead of this, when a signal processing system for composing near-distance images separately from far-distance images is provided in the image processor 15, the bypath line may be provided only in the signal processing system for processing near-distance signals.

By removing harmonic components derived from the outer aperture 42 from receiving signals of near-distance zones like this, it is possible to substantially finely draw beam widths in near-distance zones.

Also, since the fundamental frequency $f0_{out}$ of ultrasonic waves generated from the outer aperture 42 is set lower than the fundamental frequency $f0_{in}$ of ultrasonic waves generated from the inner aperture 41, an attenuation of ultrasonic waves generated from the outer aperture 42 with a long propagation distance can be reduced. The reason is that attenuation is much in high frequencies and less in low frequencies.

Further, in the case the probe has transducer elements arrayed in one-dimensional, focal points may be formed at 5 cm and 15 cm in depth.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnosis apparatus comprising:
   an ultrasonic probe having a plurality of arrayed transducer elements;
   a transmitting beam former configured to generate and to delay driving signals for driving said transducer elements so as ultrasonic waves generated from said transducer elements become in phase at different focal points at different depths at a same time;
   a receiving beam former configured to generate receiving signals based on echo signals received by said transducer elements; and
   an image processor configured to extract harmonic components from said receiving signals and generate ultrasonic image data based on said harmonic components.

2. The ultrasonic diagnosis apparatus according to claim 1, wherein said transmitting beam former generates said driving signals so as ultrasonic waves generated from first transducer elements out of said transducer elements are aligned in phase at a first focal point, and ultrasonic waves generated from second transducer elements are aligned in phase at a second focal point that is deeper than said first focal point.

3. The ultrasonic diagnosis apparatus according to claim 2, wherein said second transducer elements are located outside said first transducer elements.

4. The ultrasonic diagnosis apparatus according to claim 2, wherein said first transducer elements are distributed in a circular zone with a predetermined diameter, and said second transducer elements are distributed in a ring-shaped zone surrounding the outer circumference of said circular zone.

5. The ultrasonic diagnosis apparatus according to claim 2, wherein said transmitting beam former makes different a frequency of driving signals for said first transducer elements and a frequency of driving signals for said second transducer elements from each other.

6. The ultrasonic diagnosis apparatus according to claim 2, wherein said transmitting beam former sets the frequency of driving signals for said second transducer elements lower than the frequency of driving signals for said first transducer elements.

7. An ultrasonic diagnosis apparatus comprising:
an ultrasonic probe having a plurality of arrayed transducer elements;
a transmitting beam former configured to generate and to delay driving signals for driving said transducer elements so as ultrasonic waves generated from said transducer elements become in phase at different focal points at different depths at a same time;
a receiving beam former configured to generate receiving signals based on echo signals received by said transducer elements; and
an image processor configured to extract harmonic components from said receiving signals and generate ultrasonic image data based on said harmonic components,
wherein said transmitting beam former generates said driving signals so as ultrasonic waves generated from first transducer elements out of said transducer elements are aligned in phase at a first focal point, and ultrasonic waves generated from second transducer elements are aligned in phase at a second focal point that is deeper than said first focal point,
said transmitting beam former sets the frequency of driving signals for said second transducer elements lower than the frequency of driving signals for said first transducer elements, and
said image processor has a high pass filter for removing harmonic components of ultrasonic waves from said second transducer elements out of receiving signals corresponding to zones at least shallower than said second focal point.

8. The ultrasonic diagnosis apparatus according to claim 2, wherein said transmitting beam former makes different an amplitude of driving signals for said first transducer elements and an amplitude of driving signals for said second transducer elements from each other.

9. The ultrasonic diagnosis apparatus according to claim 2, wherein said transmitting beam former sets the amplitude of driving signals for said second transducer elements higher than the amplitude of driving signals for said first transducer elements.

10. The ultrasonic diagnosis apparatus according to claim 1, wherein said transmitting beam former generates said driving signals so as ultrasonic waves generated from first transducer elements out of said transducer elements are aligned in phase at the first focal point, ultrasonic waves generated from second transducer elements are aligned in phase at the second focal point that is deeper than said first focal point, and ultrasonic waves generated from third transducer elements are aligned in phase at a third focal point that is deeper than said second focal point.

11. An ultrasonic diagnosis apparatus comprising:
an ultrasonic probe having a plurality of arrayed transducer elements;
a transmitting beam former configured to generate and to delay driving signals for driving said transducer elements so as ultrasonic waves generated from said transducer elements form different focal points at different depths at a same time;
a receiving beam former configured to generate receiving signals based on echo signals received by said transducer elements; and
an image processor configured to extract harmonic components from said receiving signals and generate ultrasonic image data based on said harmonic components.

12. An ultrasonic diagnosis apparatus comprising:
an ultrasonic probe having a plurality of arrayed transducer elements;
a transmitting beam former configured to generate driving signals for driving said transducer elements so as ultrasonic waves generated from first transducer elements out of said transducer elements are aligned in phase at a first focal point, and ultrasonic waves generated from second transducer elements are aligned in phase at a second focal point that is deeper than said first focal point;
a receiving beam former configured to generate receiving signals based on echo signals received by said first and second transducer elements; and
an image processor configured to extract harmonic components from said receiving signals and generating ultrasonic image data based on said harmonic components.

13. An ultrasonic diagnosis apparatus comprising:
an ultrasonic probe having a plurality of arrayed transducer elements;
a transmitting beam former configured to generate driving signals for driving said transducer elements so as ultrasonic waves generated from first transducer elements out of said transducer elements are aligned in phase at a first focal point, and ultrasonic waves generated from second transducer elements are aligned in phase at a second focal point that is deeper than said first focal point, and, so as ultrasonic waves generated from second transducer elements are deflected in phase by a predetermined angle from the ultrasonic waves generated from said first transducer elements at said first focal point;
a receiving beam former configured to generate receiving signals based on echo signals received by said first and second transducer elements; and
an image processor configured to generate ultrasonic image data based on said receiving signals.

14. The ultrasonic diagnosis apparatus according to claim 13, wherein said transmitting beam former generates said driving signals so as ultrasonic waves generated from said second transducer elements are aligned in phase with ultrasonic waves generated from said first transducer elements at said first focal point.

15. The ultrasonic diagnosis apparatus according to claim 13, wherein said transmitting beam former generates said driving signals so as ultrasonic waves generated from said second transducer elements are reversed in phase from ultrasonic waves generated from said first transducer elements at said first focal point.

16. An ultrasonic diagnosis apparatus comprising:
an ultrasonic probe having a plurality of arrayed transducer elements;
a transmitting beam former configured to generate and to delay driving signals for driving said transducer elements to form different focal points at different depths at a same time so as ultrasonic waves generated from first transducer elements out of said transducer elements are aligned in phase at a first focal point, and ultrasonic waves generated from second transducer elements are aligned in phase at a second focal point that is deeper than said first focal point, and, so as ultrasonic waves generated from second transducer elements are deflected in phase by a predetermined angle from the ultrasonic waves generated from said first transducer elements at said first focal point;

a receiving beam former configured to generate receiving signals based on echo signals received by said first and second transducer elements; and an image processor configured to generate ultrasonic image data based on said receiving signals, wherein said transmitting beam former shifts the phase of driving signals for said second transducer elements so as ultrasonic waves generated from said second transducer elements are deflected in phase by a predetermined angle from ultrasonic waves generated from said first transducer elements at said first focal point.

17. An ultrasonic diagnosis apparatus comprising:

an ultrasonic probe having a plurality of arrayed transducer elements;

a transmitting beam former configured to generate and to delay driving signals for driving said transducer elements to form different focal points at different depths at a same time so as ultrasonic waves generated from first transducer elements out of said transducer elements are aligned in phase at a first focal point, and ultrasonic waves generated from second transducer elements are aligned in phase at a second focal point that is deeper than said first focal point, and, so as ultrasonic waves generated from second transducer elements are deflected in phase by a predetermined angle from the ultrasonic waves generated from said first transducer elements at said first focal point;

a receiving beam former configured to generate receiving signals based on echo signals received by said first and second transducer elements; and an image processor configured to generate ultrasonic image data based on said receiving signals, wherein said transmitting beam former delays driving signals for said second transducer elements from driving signals for said first transducer elements so as ultrasonic waves generated from said second transducer elements are deflected by a predetermined angle from ultrasonic waves generated from said first transducer elements at said first focal point.

* * * * *